United States Patent
Nakamura et al.

(10) Patent No.: US 9,202,305 B2
(45) Date of Patent: Dec. 1, 2015

(54) IMAGE PROCESSING DEVICE, THREE-DIMENSIONAL IMAGE DISPLAY DEVICE, IMAGE PROCESSING METHOD AND COMPUTER PROGRAM PRODUCT

(71) Applicants: Norihiro Nakamura, Kanagawa (JP); Yoshiyuki Kokojima, Kanagawa (JP); Takeshi Mita, Kanagawa (JP)

(72) Inventors: Norihiro Nakamura, Kanagawa (JP); Yoshiyuki Kokojima, Kanagawa (JP); Takeshi Mita, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 183 days.

(21) Appl. No.: 13/727,025

(22) Filed: Dec. 26, 2012

(65) Prior Publication Data
US 2013/0286016 A1    Oct. 31, 2013

(30) Foreign Application Priority Data
Apr. 26, 2012   (JP) .................................. 2012-101820

(51) Int. Cl.
| | |
|---|---|
| G06T 15/06 | (2011.01) |
| H04N 13/00 | (2006.01) |
| A61B 6/02 | (2006.01) |
| A61B 6/00 | (2006.01) |
| A61B 8/00 | (2006.01) |
| H04N 13/04 | (2006.01) |
| A61B 8/08 | (2006.01) |

(52) U.S. Cl.
CPC ................. *G06T 15/06* (2013.01); *A61B 6/022* (2013.01); *A61B 6/466* (2013.01); *A61B 8/466* (2013.01); *A61B 8/483* (2013.01); *H04N 13/0007* (2013.01); *H04N 13/0404* (2013.01); *H04N 13/0415* (2013.01); *H04N 13/0468* (2013.01); *H04N 13/0477* (2013.01)

(58) Field of Classification Search
None
See application file for complete search history.

(56) References Cited

U.S. PATENT DOCUMENTS

| | | | | |
|---|---|---|---|---|
| 5,229,935 | A | * | 7/1993 | Yamagishi et al. ........... 600/425 |
| 6,064,424 | A | | 5/2000 | Van Berkel et al. |
| 2004/0150583 | A1 | * | 8/2004 | Fukushima et al. ............. 345/6 |

(Continued)

FOREIGN PATENT DOCUMENTS

| | | |
|---|---|---|
| JP | 2007-200307 | 8/2007 |
| JP | 4672461 | 1/2011 |
| JP | 2011-130922 | 7/2011 |

OTHER PUBLICATIONS

Van Berkel; "Image Preparation for 3D-LCD", Download Address: http://94.23.146.173/ficheros/bb9c79eb94712071424a648640c04df.pdf, pp. 1-8.

Notice of Rejection issued by the Japanese Patent Office on Jun. 3, 2014, for Japanese Patent Application No. 2012-101820, and English-language translation thereof.

(Continued)

*Primary Examiner* — Daniel Hajnik
(74) *Attorney, Agent, or Firm* — Finnegan, Henderson, Farabow, Garrett & Dunner, L.L.P.

(57) ABSTRACT

According to an embodiment, an image processing device generates a three-dimensional image to be displayed on a display unit. The display unit includes a display element unit that has pixels each containing a plurality of sub-pixels arranged thereon and a ray control element unit that controls emission directions of rays emitted from the sub-pixels. The image processing device includes a first acquiring unit configured to acquire three-dimensional data for generating the three-dimensional image; and a generating unit configured to calculate, for each of the sub-pixels, a luminance value of the sub-pixel on the basis of an emission direction of a ray emitted from the sub-pixel through the ray control element unit and the three-dimensional data to generate the three-dimensional image.

8 Claims, 8 Drawing Sheets

(56) References Cited

U.S. PATENT DOCUMENTS

| | | | |
|---|---|---|---|
| 2005/0225502 A1* | 10/2005 | Nam et al. | 345/55 |
| 2008/0225114 A1* | 9/2008 | De Zwart et al. | 348/51 |
| 2009/0282429 A1* | 11/2009 | Olsson et al. | 725/10 |
| 2011/0158380 A1 | 6/2011 | Tsukagoshi et al. | |
| 2012/0019529 A1* | 1/2012 | Kimpe | 345/419 |
| 2012/0120065 A1* | 5/2012 | Kim et al. | 345/419 |

OTHER PUBLICATIONS

Nakamura et al., U.S. Appl. No. 14/272,956, filed May 8, 2014.
Japanese Patent Office, Notice of Rejection issued in Japanese Application 2012-101820, Mailed Feb. 3, 2015, 1 pages.
Van Berkel; "Image Preparation for 3D-LCD", Download Address: http://94.23.146.173/ficheros/bb9c79eb94712071424a648640c04df.pdf, pp. 1-8, 1999.

* cited by examiner

TRANSFORMATION MODEL FROM
PARALLAX TO DEPTH

IMAGE PROCESSING DEVICE, THREE-DIMENSIONAL IMAGE DISPLAY DEVICE, IMAGE PROCESSING METHOD AND COMPUTER PROGRAM PRODUCT

CROSS-REFERENCE TO RELATED APPLICATION

This application is based upon and claims the benefit of priority from Japanese Patent Application No. 2012-101820, filed on Apr. 26, 2012; the entire contents of which are incorporated herein by reference.

FIELD

Embodiments described herein relate generally to an image processing device, a three-dimensional image display device, an image processing method, and a computer program product.

BACKGROUND

In recent years, in the field of medical diagnostic imaging systems such as X-ray computed tomography (CT) scanners, magnetic resonance imaging (MRI) machines and ultrasonic diagnostic scanners, devices capable of generating three-dimensional medical imaging volume data have been in practical use. In addition, technologies for rendering volume data from an arbitrary viewpoint have been in practical use, and it has recently been attempted to display volume data three-dimensionally on a three-dimensional image display device.

With a three-dimensional image display device, viewers can view three-dimensional images with naked eyes without using special glasses. Such a three-dimensional image display device displays a plurality of images (each of which will be hereinafter referred to as a parallax image) from different viewpoints and controls rays for these parallax images with a ray control element unit such as a parallax barrier or a lenticular lens. In this process, an image to be displayed needs to be one obtained by rearrangement so that intended images are observed in intended directions when viewed through the ray control element unit. A method for the arrangement will be referred to below as pixel mapping, and various pixel mapping methods have been known in related art. Rays controlled by the ray control element unit and by pixel mapping therefor are guided to the eyes of a viewer, who can then recognize a three-dimensional image if the viewer is at an appropriate viewpoint. A zone that enables a viewer to view a three-dimensional image in this manner is referred to as a viewing zone.

The number of viewpoints in generating parallax images is determined in advance, which is typically not sufficient for determining luminance information of all pixels of a display panel. Accordingly, for pixels to which parallax images associated with respective predetermined viewpoints are not assigned (for pixels for which luminance information is not determined from parallax images), the luminance information thereof needs to be determined by performing interpolation using parallax images for a nearest viewpoint.

Since parallax images for different viewpoints are blended as a result of the interpolation, a problem occurs such as generation of a multi-layered image that is observed as having two or more overlapping edge portions where one edge portion should originally be observed or blurring of the entire image.

DETAILED DESCRIPTION

According to an embodiment, an image processing device generates a three-dimensional image to be displayed on a display unit. The display unit, includes a display element unit that has pixels each containing a plurality of sub-pixels arranged thereon and a ray control element unit that controls emission directions of rays emitted from the sub-pixels. The image processing device includes a first acquiring unit configured to acquire three-dimensional data for generating the three-dimensional, image; and a generating unit configured to calculate, for each of the sub-pixels, a luminance value of a sub-pixel on the basis of an emission direction of a ray emitted from the sub-pixel through the ray control element unit and the three-dimensional data to generate the three-dimensional image.

Embodiments of an image processing device, a method therefor and a computer program product therefor, and a three-dimensional image display device will be described below in detail with reference to the accompanying drawings.

First Embodiment

Figure 1:
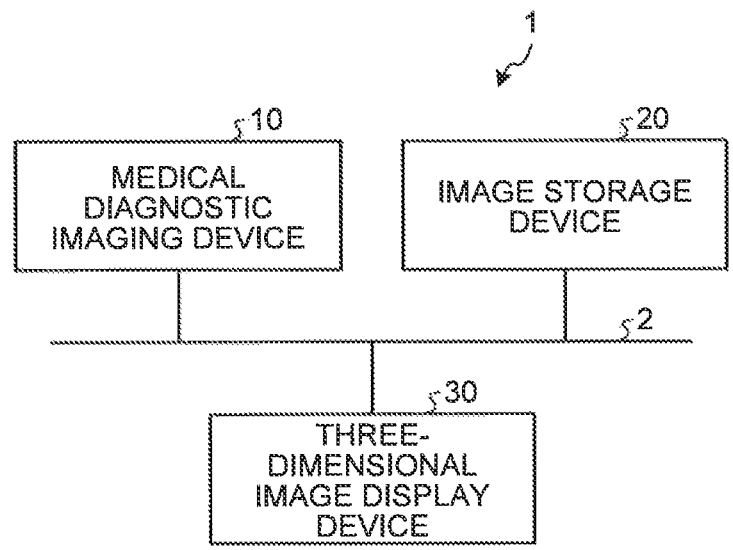
FIG. 1 is a diagram illustrating an exemplary configuration of an image display system according to an embodiment.

FIG. 1 is a block diagram illustrating an exemplary configuration of an image display system 1 according to the present embodiment. As illustrated in FIG. 1, the image display system 1 includes a medical diagnostic imaging device 10, an image storage device 20 and a three-dimensional image display device 30. The devices illustrated in FIG. 1 are in a state in which the devices can directly or indirectly communicate through a communication network 2, and the devices can mutually transmit/receive medical images and the like. Any type of communication network 2 may be used, and the devices may be in a configuration in which the devices can mutually communicate via a local area network (LAN) installed in a hospital, for example. Alternatively, the devices may be in a configuration in which the devices can mutually communicate via a network (cloud) such as the Internet, for example.

The image display system 1 generates a three-dimensional image, which is an image that can be viewed stereoscopically by a viewer, from three-dimensional medical imaging volume data generated by the medical diagnostic imaging device 10. The image display system 1 provides medical images that can be viewed stereoscopically for doctors and medical technologists working at the hospital by displaying the generated three-dimensional image on a display unit. A three-dimensional image is an image that can be stereoscopically viewed by a viewer. The devices will be sequentially described below.

The medical diagnostic imaging device 10 is a device that can generate three-dimensional medical imaging volume data. Examples of the medical diagnostic imaging device 10 include X-ray diagnostic equipment, an X-ray CT scanner, an MRI machine, an ultrasonic diagnostic scanner, a single photon emission computed tomography (SPECT) scanner, a positron emission computed tomography (PET) scanner, an SPECT-CT scanner integrating an SPECT scanner and an X-ray CT scanner, a PST-CT scanner integrating a PET scanner and an X-ray CT scanner, or a group of these, devices.

Figure 2:
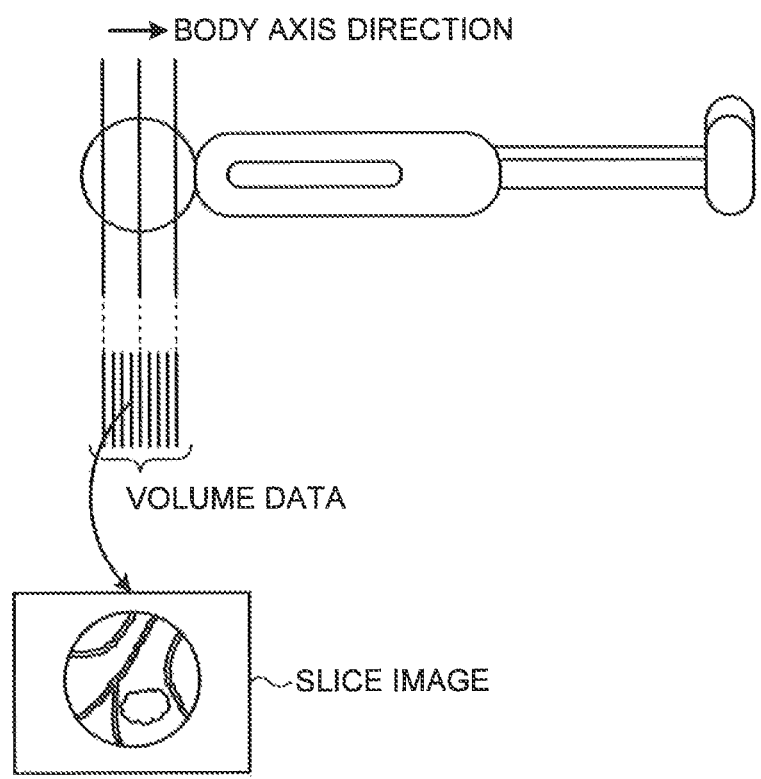
FIG. 2 is a diagram for explaining an example of volume data according to the embodiment.

The medical diagnostic imaging device 10 generates volume data by capturing a subject. For example, the medical diagnostic imaging device 10 collects data such as projection data and MR signals by capturing a subject and reconstructs multiple (300 to 500, for example) slice images (section images) along the body axis direction of the subject from the collected data to generate volume data. As illustrated in FIG. 2, a plurality of slice images captured along the body axis direction of the subject is the volume data. In the example of FIG. 2, volume data of the "brain" of the subject are generated. Alternatively, projection data, MR signals or the like themselves of the subject captured by the medical diagnostic imaging device 10 may be the volume data. The volume data generated by the medical diagnostic imaging device 10 include images of objects such as bones, blood vessels, nerves and tumors to be observed in medical practice. The volume data may also include data representing isosurfaces of volume data by a set of geometric elements such as a polygon and a curved surface.

The image storage device 20 is a database that stores medical images. Specifically, the image storage device 20 stores and maintains volume data transmitted from the medical diagnostic imaging device 10.

The three-dimensional image display device 30 is a device that generates and displays a three-dimensional image of the volume data generated by the medical diagnostic imaging device 10. The three-dimensional image display device 30 may employ a 3D display system such as an integral imaging system (II system) or a multi-view system. Examples of the three-dimensional image display device 30 include a TV set and a PC with which a viewer can view a three-dimensional image with naked eyes.

While an example in which the three-dimensional image display device 30 generates a three-dimensional image from the volume data generated by the medical diagnostic imaging device 10 will be described below, the generation of a three-dimensional image is not limited thereto and any type of three-dimensional data may be used to generate a three-dimensional image by the three-dimensional image display device 30. Three-dimensional data is data that can represent the shape of a three-dimensional object and can include a space partitioning model or a boundary representation model such as volume data. A space partitioning model refers to a model representing a three-dimensional object by using grids into which a space is partitioned, for example. A boundary representation model refers to a model representing a three-dimensional object by representing boundaries of a region occupied by the three-dimensional object, for example.

Figure 3:
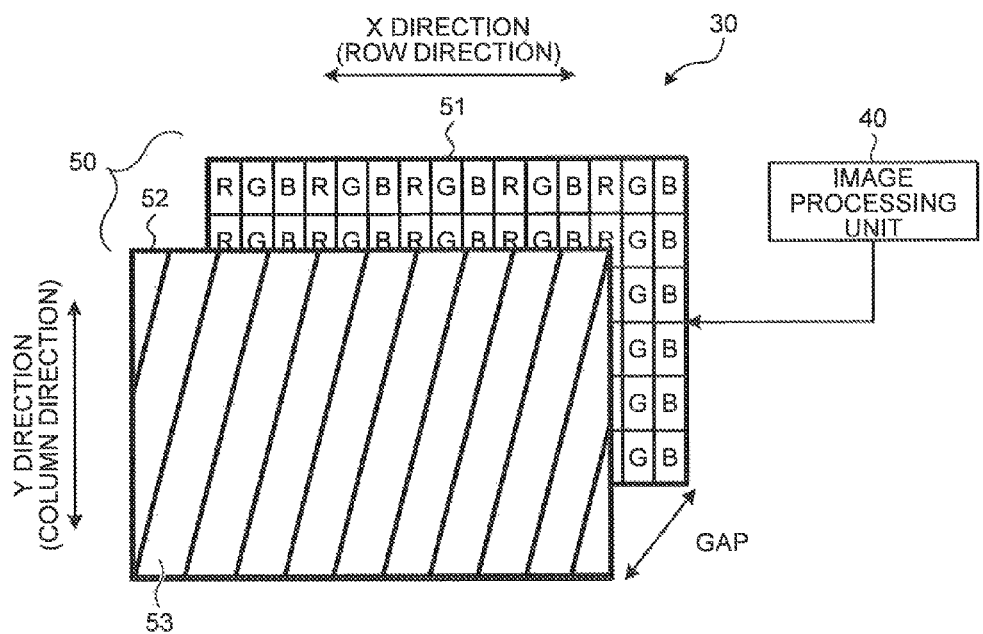
FIG. 3 is a diagram illustrating an exemplary configuration of a three-dimensional image display device according to the embodiment.

FIG. 3 is a block diagram illustrating an exemplary configuration of the three-dimensional image display device 30. As illustrated in FIG. 3, the three-dimensional image display device 30 includes an image processing unit 40 and a display unit 50. The image processing unit 40 and the display unit 50 may be in a configuration connected via a communication network (network). The image processing unit 40 generates a three-dimensional image to be displayed on the display unit 50. In the first embodiment, the image processing unit 40 generates a three-dimensional image of volume data generated by the medical diagnostic imaging device 10. Details of the image processing unit 40 will be described later.

As illustrated in FIG. 3, the display unit 50 includes a display element unit 51 and a ray control element unit 52. A viewer views a three-dimensional image displayed on the display unit 50 by viewing the display element unit 51 through the ray control element unit 52. For example, when a viewer views the display unit 50, different pictures are input to the left eye and the right eye of the viewer, which allows the viewer to recognize a three-dimensional image.

The display element unit 51 displays a three-dimensional image. The display element unit 51 has an array of pixels each containing a plurality of sub-pixels. More specifically, a plurality of sub-pixels with different colors (R, G and B, for example) is arranged in a matrix in the X direction (row direction) and the Y direction (column direction) on the display element unit 51. In the example of FIG. 3, one pixel is constituted by sub-pixels of R, G, and B. The sub-pixels are arranged such that a pattern in an order of R (red), G (green) and B (blue) is repeated in the X direction and the same color components are arranged in the Y direction. The display element unit 51 may be a direct-view two-dimensional display, such as an organic electro luminescence (organic EL), a liquid crystal display (LCD), a plasma display panel (PDF), or a projection display. Alternatively, the display element unit 51 may include a backlight. Hereinafter, the display element unit 51 may also be referred to as a panel.

The ray control element unit 52 controls the directions of rays emitted from the sub-pixels of the display element unit 51. The ray control element unit 52 has a plurality of linearly extending optical openings 53 arranged along the X direction. In the example of FIG. 3, the ray control element unit 52 is lenticular sheeting having a plurality of cylindrical lenses (serving as the optical openings 53 for emitting rays) that is arrayed, however the ray control element unit 52 is not limited thereto and may be a parallax barrier having a plurality of slits that is arrayed, for example. The display element unit 51 and the ray control element unit 52 have a certain distance (gap) therebetween. The ray control element unit 52 is arranged so that the extending direction of the optical, openings 53 thereof has a predetermined slope with respect to the Y direction (column direction) of the display element unit 51.

Figure 4:
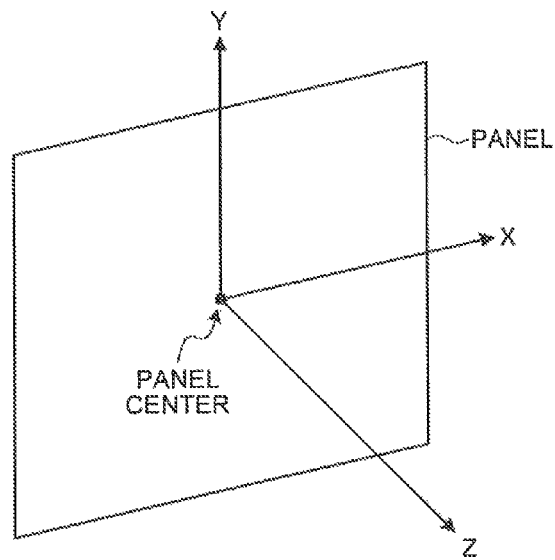
FIG. 4 is a diagram, illustrating an example of a coordinate system in which the center of a panel is the origin.

In the present embodiment, as illustrated in FIG. 4, the center of a display surface (display screen) of the panel is set as the origin, the horizontal direction of the display surface is set as the X axis, the vertical direction of the display surface is set as the Y axis, and the normal direction of the display surface is set as the Z axis. In the present embodiment, the height direction refers to the Y-axis direction. Note that the manner in which coordinates are set in the real space is not limited to the above.

Figure 5:
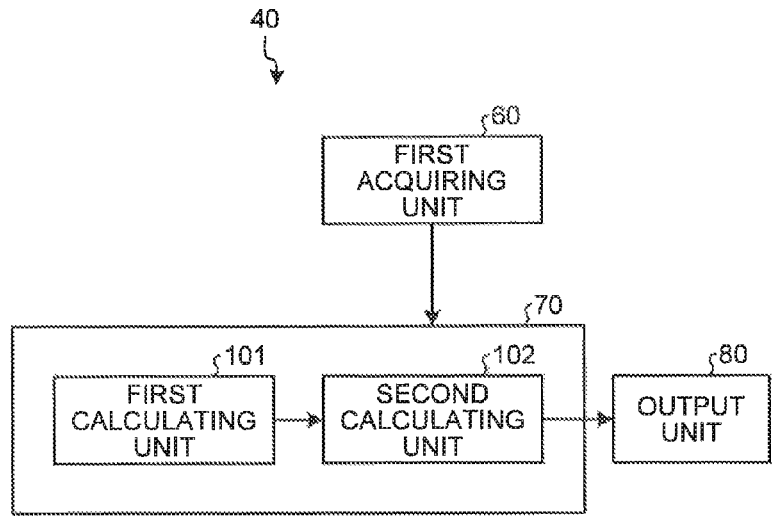
FIG. 5 is a diagram illustrating an exemplary configuration of an image processing unit according to a first embodiment.

Next, details of the image processing unit 40 will be described. FIG. 5 is a block diagram illustrating an exemplary configuration of the image processing unit 40. As illustrated in FIG. 5, the image processing unit 40 includes a first acquiring unit 60, a generating unit 70, and an output unit 80.

The first acquiring unit 60 accesses the image storage device 20 to acquire volume data generated by the medical diagnostic imaging device 10. The volume data may include position information for locating organs such as bones, blood vessels, nerves and tumors. Any form of position information may be used, such as a form in which identification information identifying the type of an organ and a group of voxels belonging to the organ are managed in association with each other or a form in which identification information identifying the type of an organ to which, voxels belong is added to each of the voxels contained in volume data. The volume data may also contain information relating to coloring and transparency in rendering each organ.

Alternatively, a memory storing the generated volume data may be provided in the medical diagnostic imaging device 10 instead of providing the image storage device 20, for example. In this case, the first acquiring unit 60 accesses the medical diagnostic imaging device 10 to acquire volume data. In other words, the first acquiring unit 60 acquires three-dimensional data for generating a three-dimensional image to be displayed on the display unit 50.

The generating unit 70 generates a three-dimensional image by calculating, for each sub-pixel, a luminance value of the sub-pixel by using a ray number representing the direction in which a ray from the sub-pixel is emitted through the ray control element unit 52 and the volume data acquired by the first acquiring unit 60. As illustrated in FIG. 5, the generating unit 70 includes a first calculating unit 101 and a second calculating unit 102.

The first calculating unit 101 calculates, for each sub-pixel, ray information that can identify a rendering ray that is a ray passing through a viewpoint position corresponding to the sub-pixel and used for calculation of the luminance value of the sub-pixel. Note that the ray number of each sub-pixel is determined when the display unit 50 is designed. The ray number of each sub-pixel is determined as a number representing the direction in which a ray from the sub-pixel travels through the optical openings 53 when the number of reference viewpoints is N, a region having a horizontal width $X_n$ and a vertical width $Y_n$ with reference to the X axis with respect to the extending direction of the optical openings 53 is defined as a region in which an elemental image containing pixels of N viewpoints is displayed (hereinafter may also be referred to as a 3D pixel region representing one pixel of a three-dimensional image) and the directions are sequentially defined such that the ray travel direction in which a ray travel that is emitted from a position corresponding to a boundary that is the farthest in the negative direction of the X axis in a 3D pixel region travels is 0, the direction in which a ray travels that is emitted from a position away by $X_n/N$ from the boundary is 1, and so on.

In the first embodiment, since the horizontal width of lenses and barriers serving as the optical openings 53 is equal to $X_n$, rays having the same ray number are substantially parallel rays and the same ray numbers in 3D pixel regions represent the same direction. In this case, rays having the same ray number can be considered to be focused on infinity from the panel.

Figure 6:
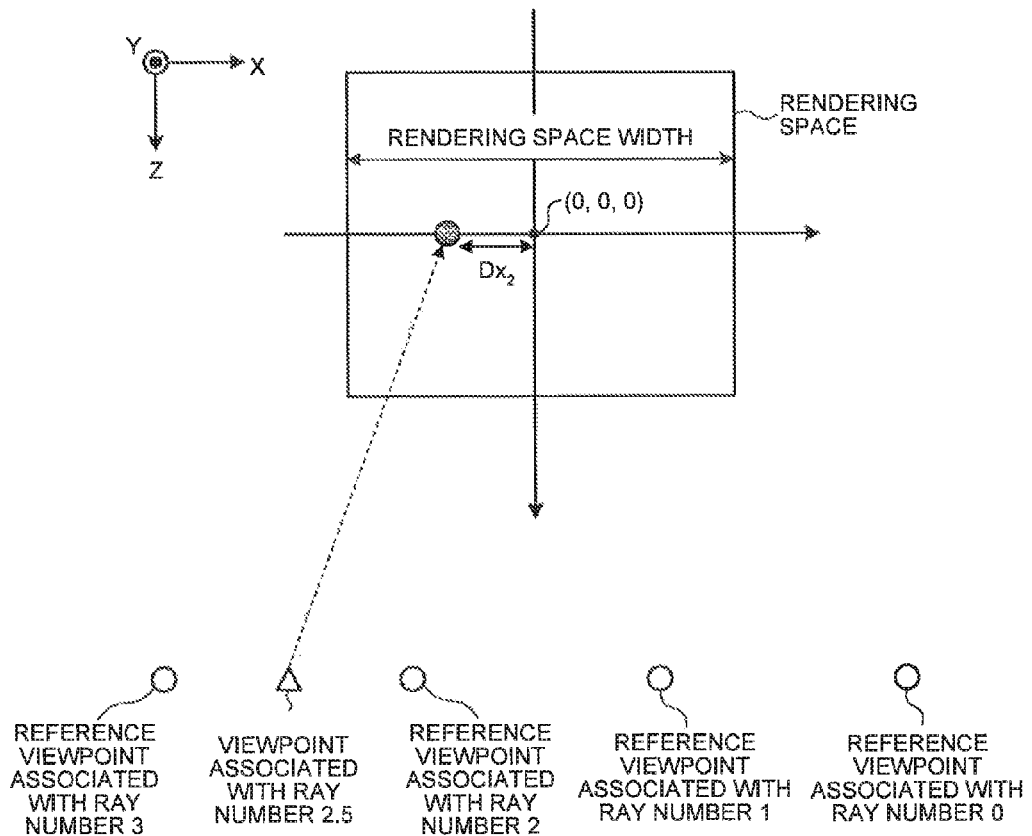
FIG. 6 is a diagram for explaining association between reference viewpoints and ray numbers.

Reference viewpoints refer to positions of a plurality of viewpoints (cameras in the field of computer graphics) defined at certain intervals in a space to be rendered (hereinafter referred to as a "rendering space"). A method for associating the reference viewpoints with ray numbers can be sequentially associating reference viewpoints starting from a rightmost one in a state facing the panel with ray numbers starting from a smallest one, for example. Thus, in this case, a rightmost reference viewpoint is associated with the ray number 0 and a second, rightmost reference viewpoint is associated with the ray number 1. As illustrated in FIG. 6, the first calculating unit 101 associates a reference viewpoint with an integer ray number. In the example of FIG. 6, it can also be considered that a physical ray direction identified by an integer ray number is corrected according to a coordinate system defining three-dimensional data (volume data in this example) and that a reference viewpoint associated with the corrected ray direction is associated with the ray number. Note that the parallax is larger and a protrusion (a depth) when a final three-dimensional image is displayed is larger as the interval between reference viewpoints is larger. Accordingly, the protrusion can be controlled similarly to the related art by adjusting the interval between reference viewpoints.

While an example in which the horizontal width of lenses or barriers serving as the optical openings 53 is equal to $X_n$ is described in the first embodiment, embodiments are not limited thereto. In a case where the horizontal width of lenses or barriers serving as the optical openings 53 is not equal to $X_n$, the ray numbers are serial numbers only in a 3D pixel region and the same numbers in different 3D pixel regions do not represent the same direction. When rays having the same ray number are collected, the rays will focus on a point (focal point) that is different for each ray number. In other words, the ray number in this case has the same value (number) in units of rays focusing on a certain focal point and each focal point is indicative of a different value.

An example of calculation of the ray information by the first calculating unit 101 will be described below. In the first embodiment, the ray numbers of the sub-pixels are determined in advance and it is a precondition that the first calculating unit 101 is capable of knowing the ray numbers of the sub-pixels. While an example in which the ray information of a sub-pixel with a ray number "2.5" is calculated will be described below, the method for calculating ray information for other sub-pixels is the same.

First, the first calculating unit 101 identifies a viewpoint position of a sub-pixel for which ray information is to be calculated (hereinafter may also be referred to as a "sub-pixel to be calculated") on the basis of the ray number of the sub-pixel. If the ray number of the sub-pixel is an integer, the first calculating unit 101 identifies the reference viewpoint associated with the ray number as the viewpoint position associated with the sub-pixel. If the ray number of the sub-pixel has a fractional value, on the other hand, the first calculating unit 101 identifies the viewpoint position associated with the sub-pixel by performing linear interpolation on the basis of reference viewpoints in the vicinity. Since the ray number of the sub-pixel to be calculated is 2.5, the first calculating unit 101 can identify the viewpoint position associated with the ray number 2.5 by performing linear interpolation using a reference viewpoint associated with a ray number of 2 and a reference viewpoint associated with a ray number of 3 as illustrated in FIG. 6. The viewpoint position identified as described above will be the position through which a rendering ray for the sub-pixel to be calculated (the sub-pixel with the ray number 2.5 in this example) (starting position of the rendering ray, for example). In this example, it can also be considered that the first calculating unit 101 identifies, for each sub-pixel, the viewpoint position associated with the direction obtained by correcting the direction (physical ray direction) represented by the ray number of the sub-pixel according to a coordinate system of three-dimensional data as the viewpoint position of the sub-pixel.

Figure 7:
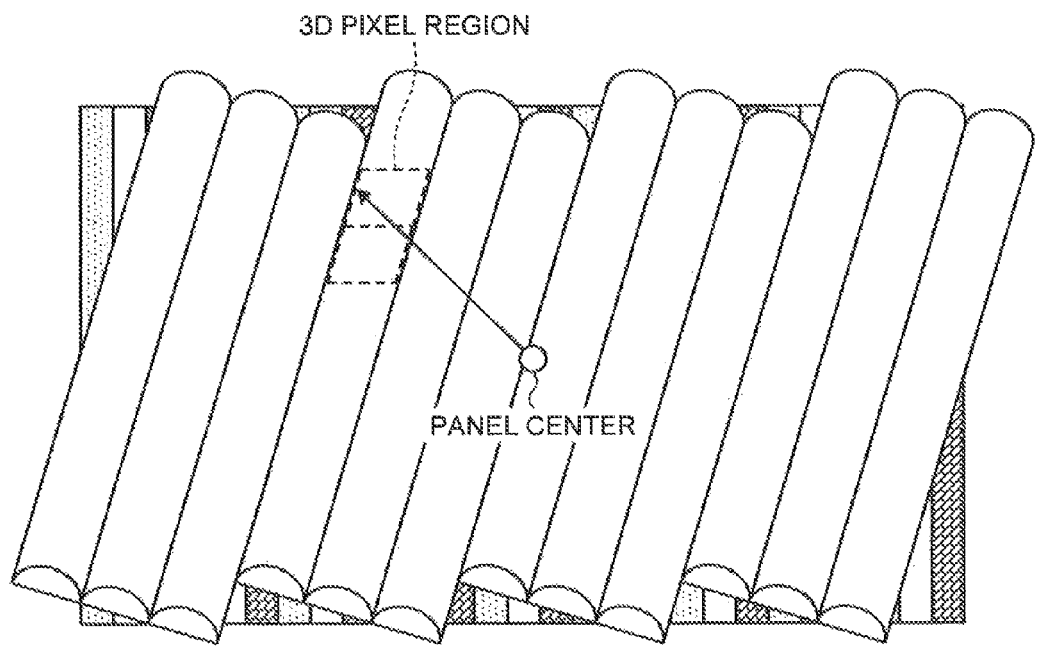
FIG. 7 is a diagram illustrating an example of a vector from the panel center to a 3D pixel region.
Figure 8:
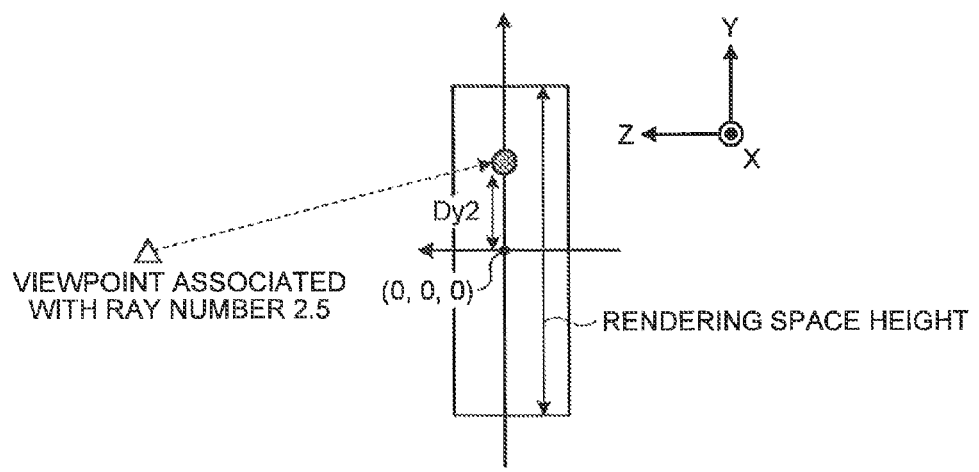
FIG. 8 is a schematic diagram of a case where the panel is viewed in the X-axis direction.

Next, the first calculating unit 101 obtains a vector $Dv_1 = (Dx_1, Dy_1)$ from the panel center to a left end of a 3D pixel region containing the sub-pixel to be calculated as illustrated in FIG. 7. The left end of the 3D pixel region in this case refers to a left end on a Y axis that is the same as the Y axis of the sub-pixel to be calculated. Next, the first calculating unit 101 obtains a vector $Dv_2$ representing the position of the left end of the 3D pixel region containing the sub-pixel to be calculated in the rendering space. $Dx_2$ illustrated in FIG. 6 represents an x component of the vector $Dv_2$ and $Dy_2$ illustrated in FIG. 8 represents a y component of the vector $Dv_2$.

It is considered here that the lateral width of the rendering space corresponds to the width in the X-axis direction of the panel, the height of the rendering space corresponds to the width in the Y-axis direction of the panel and the origin (0, 0, 0) of the rendering space corresponds to the center of the panel. The first calculating unit 101 obtains the x component $(Dx_2)$ of $Dv_2$ by normalizing the x component $(Dx_1)$ of $Dv_1$ with the width in the X-axis direction of the panel and multiplying the normalized value by the lateral width of the rendering space. The first calculating unit 101 also obtains the y component $(Dy_2)$ of $Dv_2$ by normalizing the y component $(Dy_1)$ of $Dv_1$ with the width in the Y-axis direction of the panel and multiplying the normalized value by the height of the rendering space. $Dv_2 = (Dx_2, Dy_2)$ obtained as described above will be an end point position of the rendering ray used for calculation of the luminance value of the sub-pixel to be calculated, and the first calculating unit 101 can obtain a directional vector of the rendering ray for the sub-pixel to be calculated from the viewpoint position (starting point position of the ray) associated with the sub-pixel to be calculated, and $Dv_2$. Thus, the viewpoint position associated with the sub-pixel to be calculated and $Dv_2$ calculated as described above can be regarded as ray information allowing identifying the rendering ray for the sub-pixel to be calculated to be identified. The first calculating unit 101 calculates the ray information, of each sub-pixel as described, above.

While a case in which the projection method in rendering volume data is perspective project is assumed in the calculation of the ray information described above, the projection method in rendering is not limited thereto and orthogonal projection may alternatively be used instead of perspective projection. In this case, $Dv_2$ may be added to the starting point position of the ray. Alternatively, a combination of orthogonal projection and perspective projection can also be used. In this case, only a component, to be subjected to perspective projection out of the components of $Dv_2$ may be added to the starting point position of the ray.

While one lens or barrier is used as the optical opening 53 in the description of the first embodiment, the optical opening 53 is not limited thereto and it is also possible to consider a plurality of lenses (barriers) collectively as one virtual lens (barrier) and regard the virtual lens (barrier) as the optical opening 53. In this case, the same processes as above can be performed. Moreover, while the left end on the same Y coordinate as that of the sub-pixel to be calculated in 3D pixel region containing the sub-pixel, to be calculated is used as a reference in the present embodiment, the reference is not limited thereto. Alternatively, a right end on the same Y coordinate as that of the sub-pixel to be calculated may be used as a reference or the center obtained by averaging position coordinates of the left end and the right end may be used as a reference. In other words, a point representing a partial region having the same Y coordinate as that of the sub-pixel to be calculated in the 3D pixel region can be used as a reference. In addition, while a shape in which a lens serving as the optical opening 53 projects toward the viewer (that is, a shape in which a convex face of the lens faces the viewer) is described as an example in the example of FIG. 7, the lens is not limited thereto and a shape in which the lens projects toward the panel opposite to the side of the viewer (that is, a shape in which a convex face of the lens faces the panel) may be used.

Furthermore, while a case in which the panel center corresponds to the origin (0, 0, 0) of the rendering space is described as an example in the first embodiment, the same processes as above can be performed even if the panel center and the origin (0, 0, 0) of the rendering space are misaligned, by performing appropriate coordinate transformation. Similarly, even if the lateral width of the rendering space and the width in the X-axis direction of the panel are misaligned or if the height of the rendering space and the width in the Y-axis direction of the panel are misaligned, the same processes as above can be performed by performing appropriate coordinate transformation. Furthermore, while the starting point position (viewpoint position associated with the ray number) is obtained by interpolation when the ray number has a fractional value, the interpolation method is not limited thereto and other functions may be used. For example, a non-linear function such as a sigmoid function may be used.

The description is continued referring back to FIG. 5. The second calculating unit 102 calculates, for each sub-pixel, the luminance value of the sub-pixel by using the ray information calculated, by the first calculating unit 101 and the volume data acquired by the first acquiring unit 60. As a result, rendering and mapping of the volume data are simultaneously performed and a three-dimensional image in which the volume data can be stereoscopically viewed is generated.

More specifically, the second calculating unit 102 calculates, for each sub-pixel, the luminance value of the sub-pixel on the basis of color information of a portion where the rendering ray identified by the ray information of the sub-pixel and the volume data intersect. Examples of the method for obtaining the luminance value of each sub-pixel that can foe used include ray casting and ray tracing widely known in the field of computer graphics. Ray casting is a method of tracing a ray (rendering ray) from an viewpoint and integrating color information at an intersection of the ray and three-dimensional data such as volume data to determine the luminance value of a sub-pixel, ahead of the ray and perform rendering, while ray tracing is a method taking reflected light into account in addition thereto. Detailed description will not be provided. In addition, rendering may be performed by using ray casting, ray tracing or the like similarly to the above also in a case where another model (an example of three-dimensional data) that is in the field of computer graphics such as boundary representation model is used instead of volume data.

The output unit 80 outputs (displays) the three-dimensional image generated by the generating unit 70 to (on) the display unit 50.

Figure 9:
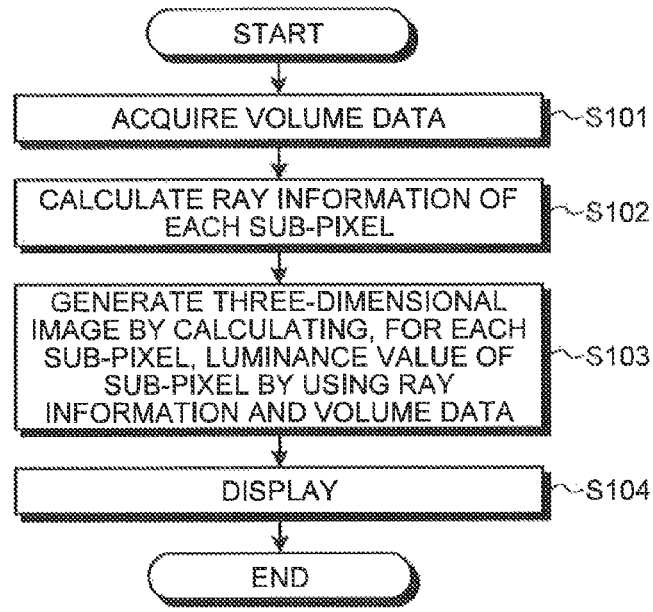
FIG. 9 is a flowchart illustrating an exemplary operation of a three-dimensional image display device, according to the first embodiment.

Next, an exemplary operation of the three-dimensional image display device 30 according to the first embodiment will be described with reference to FIG. 9. FIG. 9 is a flowchart illustrating an exemplary operation of the three-dimensional image display device. First, in step S101, the first acquiring unit 60 accesses the image storage device 20 to acquire volume data generated by the medical diagnostic imaging device 10. In step S102, the first calculating unit 101 calculates, for each sub-pixel, ray information capable of identifying a rendering ray of the sub-pixel by using the ray number of the sub-pixel. In step S103, the second calculating unit 102 calculates, for each sub-pixel, the luminance value of the sub-pixel by using the ray information of the sub-pixel and the volume data acquired in step S101 to generate a three-dimensional image. In step S104, the output unit 80 displays the three-dimensional image generated by the generating unit 70 on the display unit 50.

As described above, in the present embodiment, ray information capable of identifying a rendering ray of the sub-pixel is calculated for each sub-pixel on the basis of the ray number of the sub-pixel. Then, for each sub-pixel, the luminance value of the sub-pixel is calculated by performing ray casting or the like using the ray information of the sub-pixel and the volume data. Thus, in the present embodiment, since the luminance value of each sub-pixel is directly calculated without performing a process of interpolating parallax images, it is possible to prevent occurrence of multi-layered images and blurring. According to the first embodiment, the quality of three-dimensional images to be provided to viewers can therefore be improved.

Modification of First Embodiment

For example, three-dimensional data from which a three-dimensional image is generated by the image processing unit 40 may be in a configuration combining an image at one viewpoint (hereinafter referred to as a "reference image") and depth data (data representing depth values of pixels in the reference image) associated thereto. In this case, the generating unit 70 calculates the luminance value of a sub-pixel by parallel-translating the reference image according to the ray number of the sub-pixel and the depth data and on the basis of the reference image after the parallel translation. Functions of each of the first calculating unit 101 and the second calculating unit 102 in this case will be described below.

Basic functions of the first calculating unit 101 are the same as those in the first embodiment. In the case of the present modification, the rendering ray of each sub-pixel need not be identified, and the first calculating unit 101 obtains, for each sub-pixel, the viewpoint position associated with the sub-pixel and the distance (vector $Dv_1$) thereof from the panel center and obtains a vector $Dv_2$ representing the position of a 3D pixel region containing the sub-pixel in the rendering space.

The second calculating unit 102 calculates, for each sub-pixel, the luminance value of the sub-pixel on the basis of the ray number of the sub-pixel, the vector $Dv_2$ representing the position of the 3D pixel region containing the sub-pixel in the rendering space, the reference image and the depth data. More specifically, the calculation is performed as follows. An example of a case where the reference image is an image associated with the ray number 0 (an image associated with the reference viewpoint 0), the lateral width of the reference image corresponds to the width of the rendering space, the vertical width of the reference image corresponds to the height of the rendering space and the center of the reference image corresponds to the origin (0, 0, 0) of the rendering space (that is, a case where the panel and the reference image are arranged in the rendering space on the same scale) will be described below.

Figure 10:
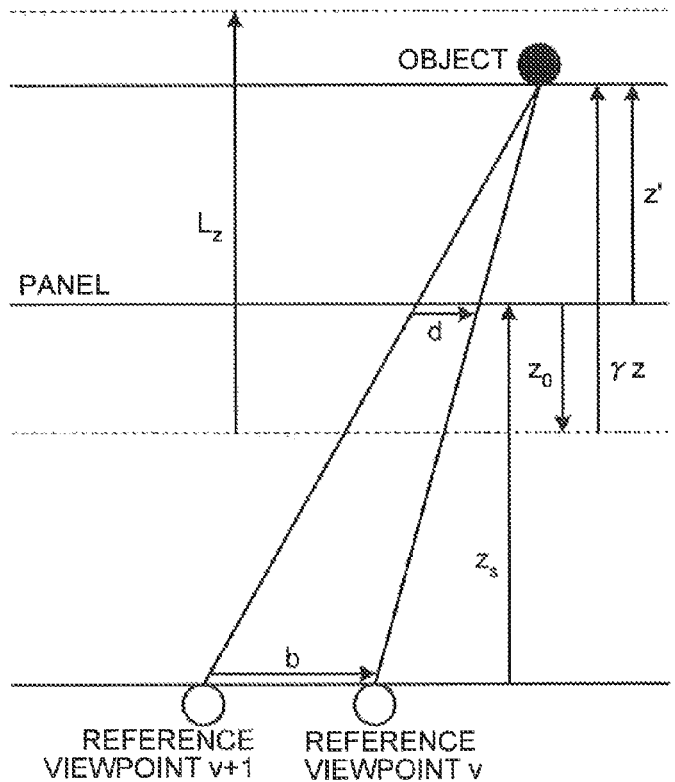
FIG. 10 is a diagram for explaining a transformation model from a parallax vector to a depth.

First, a parallax vector d of each pixel of the reference image is obtained. The parallax vector d is a vector representing which direction and how much the pixel needs to be parallel-translated to obtain a desired amount of a protrusion. As illustrated in FIG. 10, the parallax vector d at a certain pixel can be obtained by the following Equations (1).

$$\gamma = \frac{L_z}{z_{max}}$$

$$z' = \gamma z_d - z_0$$

(1)

$$d:b = z':(z_s + z')$$

$$d = b\left[\frac{z'}{z_s + z'}\right]$$

In Equations (1), $L_z$ represents a depth size in the rendering space, $z_{max}$ represents a maximum possible value of the depth data, $z_d$ represents the depth data, $z_0$ represents a protrusion distance in the rendering space, b represents a vector between reference viewpoints, and $z_s$ represents a distance from a camera position to the reference image (panel) in the rendering space.

Next, the second calculating unit 102 obtains a positional vector p2(x, y) in the rendering space of each pixel resulting from parallel translation of the reference image according to the depth data by the following Equation (2).

$$p2(x,y) = p1(x,y) - n_v d(x,y)$$ (2)

In Equation (2), x and y each represent, a coordinate in units of pixels of the reference image, $n_v$ represents the ray number of the sub-pixel for which the luminance value is to be calculated, p1(x, y) represents a positional vector in the rendering space of each vector before shifting, and d(x, y) represents a parallax vector calculated from the depth data representing the depth value of a pixel at coordinates (x, y).

Next, the second, calculating unit 102 determines one of p2(x, y) calculated as described above with position coordinates that are nearest, to those of $Dv_2$ (a vector representing the position of the 3D pixel region containing the sub-pixel for which the luminance value is to be calculated in the rendering space) described above and determines a pixel corresponding thereto. Then, the luminance value of a sub-pixel with the same color as the sub-pixel for which the luminance value is to be calculated among a plurality of sub-pixels contained in the determined pixel is the luminance value to be obtained. If there is a plurality of pixels that is nearest to $Dv_2$ described above, one pixel with the largest protrusion may be employed. The luminance value of each sub-pixel is calculated as described above.

While the parallax vectors d are obtained for all the pixels of the reference image in the present modification, the parallax vectors are not necessarily limited thereto and a pixel containing the position coordinates of $Dv_2$ may be obtained and a parallax vector d may be obtained only with pixels having the same Y coordinate (In the coordinate system of the reference image) as the pixel, for example. This is sufficient for a case in which the position of the reference viewpoint is different only in the X-axis direction. Alternatively, a pixel containing the position coordinates of $Dv_2$ may be obtained and a parallax vector d may be obtained only with pixels having the same X coordinate (in the coordinate system of the reference image) as the pixel, for example. This is sufficient for a case in which the position of the reference viewpoint is different only in the Y-axis direction. In addition, in a case where a maximum parallax vector |d| is known in the reference image, a parallax vector d may be obtained only with a pixel contained in a region of ±|d| from $Dv_2$. Furthermore, the region in which a parallax vector d is to be calculated may further be limited by combining the above.

According to the present modification, since a three-dimensional image can be generated by calculating luminance values of sub-pixels without performing a process of interpolating parallax images even when three-dimensional data includes a combination of an image associated with one viewpoint and depth data associated thereto, the quality of three-dimensional images to be provided to viewers can be improved.

Second Embodiment

Next, a second embodiment will be described. The second embodiment is different from the first embodiment described above in that a position of a viewer is acquired, parameters (hereinafter referred to as "panel parameters") relating to association between the display element unit and the ray control element unit are corrected so that the acquired position of the viewer is within a viewing zone in which the viewer can view a three-dimensional image, and ray numbers of sub-pixels are calculated using the corrected panel parameters. Specific description will be given below. Parts that are the same as those in the first embodiment described above will be designated by the same reference numerals and description thereof will not be repeated as appropriate.

Figure 11:
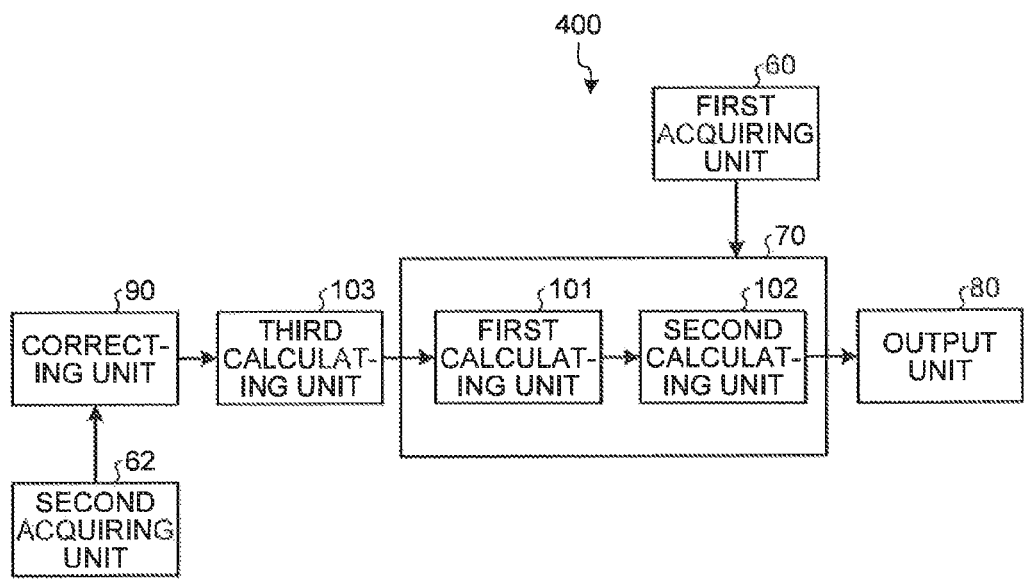
FIG. 11 is a diagram illustrating an exemplary configuration of an image processing unit according to a second embodiment.

FIG. 11 is a block diagram illustrating an exemplary configuration of an image processing unit 400 according to the second embodiment. As illustrated in FIG. 11, the image processing unit 400 is different from that in the first embodiment described above, in that the image processing unit 400 further includes a second acquiring unit 62, a correcting unit 90 and a third calculating unit 103.

The second acquiring unit 62 acquires the position of a viewer. For acquisition of the position of the viewer, a device such as a radar or a sensor as well as an imaging device such as a visible camera or an infrared camera can be used. The second acquiring unit 62 can acquire three-dimensional coordinate values representing the position of the viewer from information acquired by such devices (a captured image in a case of a camera, for example) by using a known technology.

For example, when a visible camera is used, a viewer is detected and the position of the viewer is calculated by analyzing an image obtained by capturing. As a result, the second acquiring unit 62 acquires the position of the viewer.

Alternatively, when a radar is used, a viewer is detected and the position of the viewer is calculated by processing acquired radar signals. As a result, the second acquiring unit 62 acquires the position of the viewer.

Still alternatively, for detecting a viewer in human detection and position detection, for example, any object such as a human face, a head, a whole person, and a marker that can be determined as a human may be detected. For example, the position of an eye of the viewer may be detected. Note that the method for acquiring the position of the viewer is not limited to the method described above.

Figure 12:
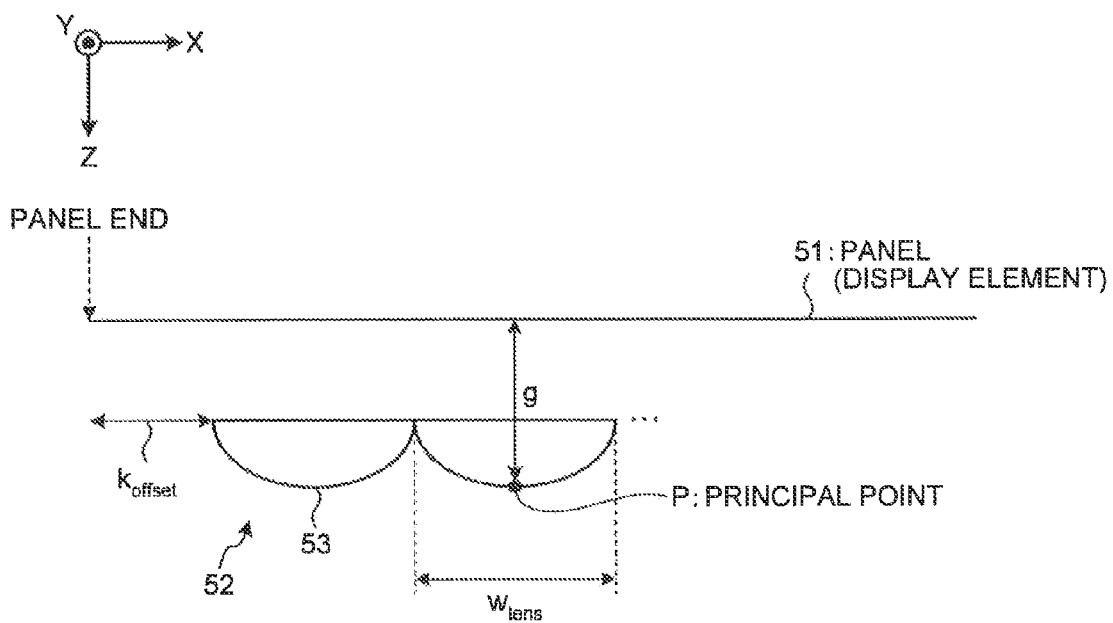
FIG. 12 is a diagram illustrating an example of panel parameters.

The correcting unit 90 corrects the panel parameters so that the position of the viewer acquired by the second acquiring unit 62 is contained in the viewing zone. The panel parameters to be corrected in the first embodiment are two parameters, which are $k_{offset}$ and $X_n$, illustrated in FIG. 12. The parameter $k_{offset}$ represents a positional difference (offset) in the X-axis direction between the panel (display element unit 51) and the ray control element unit 52. The parameter $X_n$ represents the width $X_n$ on the panel corresponding to one optical opening 53. The correcting unit 90 moves the viewing zone to a desired position by correcting $k_{offset}$ and $X_n$. More specifically, the correcting unit 90 realizes movement of the viewing zone by correcting the panel parameters as in the following Equations (3).

$$k_{offset} = k_{offset} + r_{offset}$$

$$X_n = r_{Xn} \quad (3)$$

where $r_{offset}$ represents a correction amount for $k_{offset}$; and $r_{Xn}$ represents a correction amount for $X_n$. The method for calculating these correction amounts will be described later. While a case where $k_{offset}$ is defined as a positional difference of the panel relative to the ray control element unit 52 is expressed in Equations (3), a case where $k_{offset}$ is defined as a positional difference (offset) of the ray control element unit 52 relative to the panel will, be as in the following Equations (4). Note that the correction of $X_n$ is the same as in Equations (3) described above.

$$k_{offset} = k_{offset} - r_{offset}$$

$$X_n = r_{Xn} \quad (4)$$

Figure 13:
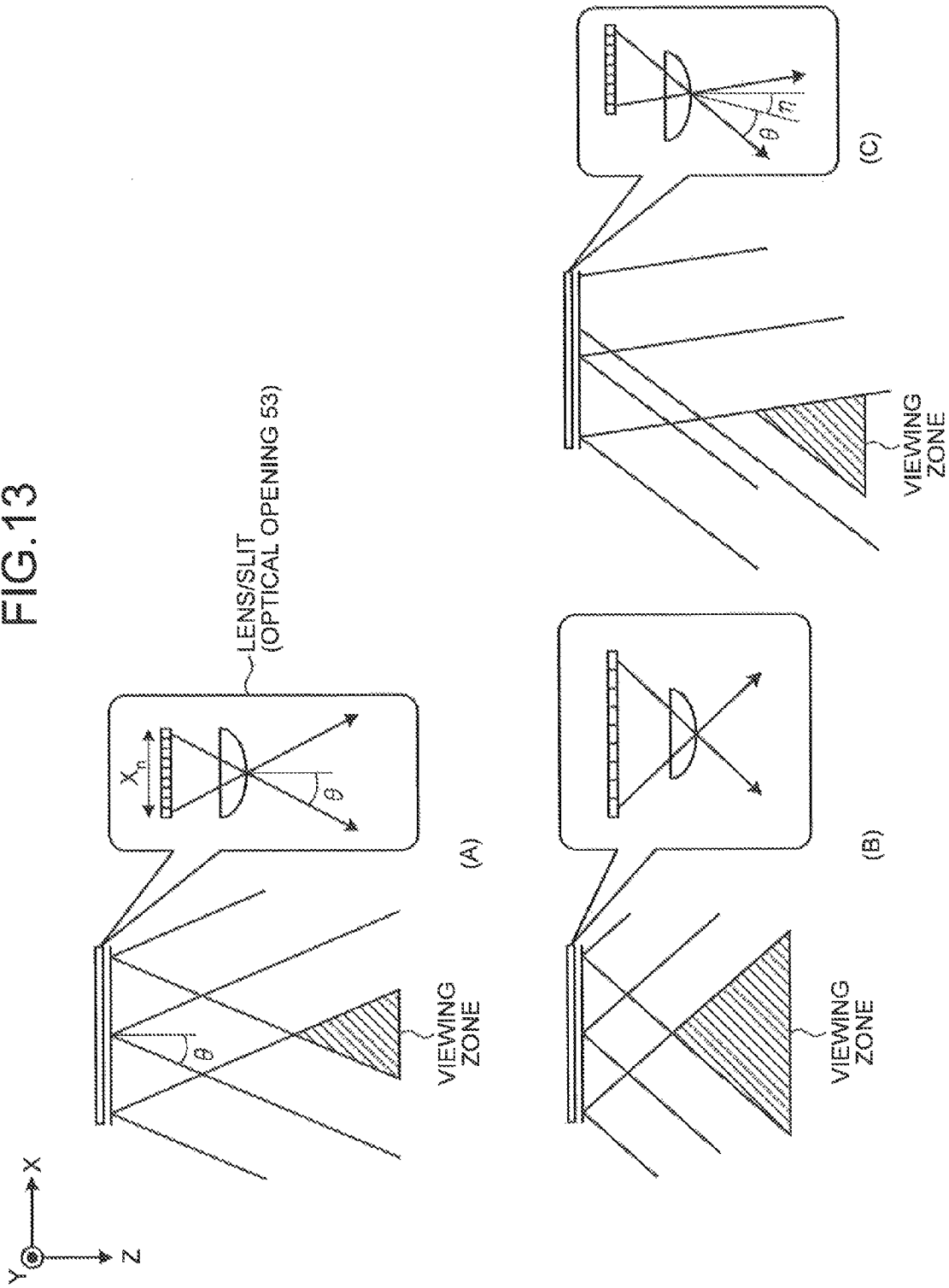
FIG. 13 is a diagram, for explaining relation between the panel parameters and viewing zones.

For example, when the relative positions of the panel and the ray control element unit 52 are shifted in the horizontal direction (X-axis direction) from a state in which the panel and the ray control element unit 52 are as illustrated in (A) of FIG. 13, the viewing zone moves to the shift direction as illustrated in (C) of FIG. 13. In the example of (C) of FIG. 13, rays are shifted to the left by η as compared to the case of (A) of FIG. 13 as a result of shifting the ray control element unit 52 (optical opening 53) to the left along the paper surface, and the viewing zone is also shifted to the left accordingly. This is equivalent to movement of a displayed image in the opposite direction when the position of the lens is considered as being fixed to the original position. In the present embodiment, it is possible to change the position of the viewing zone in the X-axis direction by setting an elemental image (setting a 3D pixel region) so that koffset that is a positional difference between the panel and the ray control element unit 52 is increased or decreased by an amount larger than a physical positional difference according to the position of the viewer.

Moreover, when the width $X_n$ on the panel corresponding to one optical opening 53 is increased as illustrated in (B) of FIG. 13 from a state in which the panel and the ray control element unit 52 are as in (A) of FIG. 13, the viewing zone comes nearer to the panel (in other words, the width of the elemental image is larger in (B) of FIG. 13 than in (A) of FIG. 13). In the second embodiment, it is possible to change the position of the viewing zone in the Z-axis direction by setting an elemental image so that the value of $X_n$ is increased or decreased.

In this manner, the position of the viewing zone can be changed in either of the X-axis direction and the Z-axis direction by appropriately correcting the panel parameters $k_{offset}$ and $X_n$. Therefore, the viewing zone can be set to meet the arbitrary position that a viewer positions. An example of the method for calculating a correction amount $r_{offset}$ for offset and a correction amount $r_{Xn}$ for $X_n$ will be presented below.

The correcting unit 90 calculates $r_{offset}$ from the X coordinate of the viewer. More specifically, the correcting unit 90 calculates $r_{offset}$ by the following Equation (5) by using the current X coordinate of the current viewer, a viewing distance L that is a distance from the viewing position to the panel (or the lens), and a gap g (see FIG. 12) that is a distance between the ray control element unit 52 (principal point P in a case of a lens) and the panel. Note that the current, viewing position is acquired by the second acquiring unit 62 and the viewing distance L is calculated from the current viewing position.

$$r_{offset} = \frac{X \times g}{L} \quad (5)$$

In addition, the correcting unit 90 calculates $r_{Xn}$ by the following Equation (6) by using the Z coordinate of the viewer. The parameter $w_{lens}$ (see FIG. 12) in Equation (6) is a width of the optical opening 53 in the X-axis direction.

$$r_{Xn} = \frac{Z+g}{L} \times w_{lens} \quad (6)$$

The description is continued referring back to FIG. 11. The third calculating unit 103 calculates the ray direction of each sub-pixel with the panel parameters corrected by the correcting unit 90. More specifically, the ray directions are sequentially defined such that the ray travel direction in which a ray travels that is emitted from, a position corresponding to a boundary that is farthest in the negative direction of the X axis in a 3D pixel region determined according to the corrected panel parameters is 0, the ray travel direction in which a ray travels that is emitted from a position away by $X_n/N$ from the boundary is 1, and so on, and ray numbers of the sub-pixels are calculated on the basis of the definitions.

Figure 14:
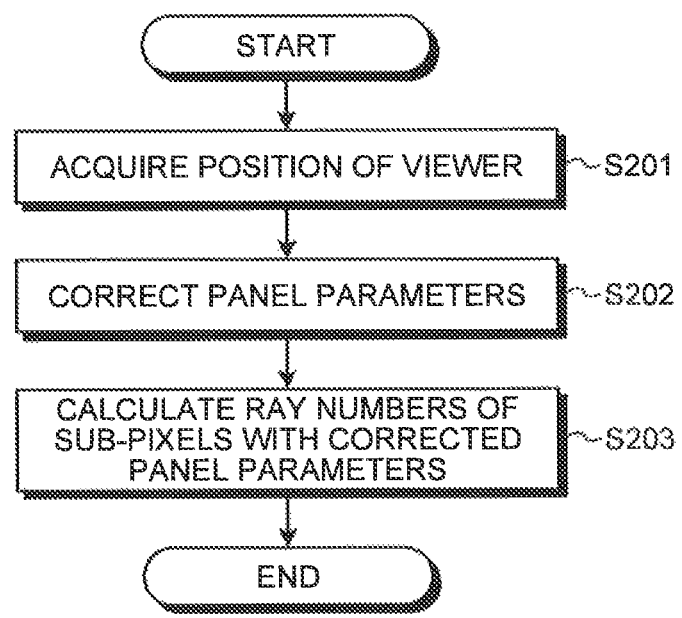
FIG. 14 is a flowchart illustrating an example of a ray number calculation process according to the second embodiment.

Since other configurations are similar to those in the first embodiment described above, detailed description thereof will not be repeated. FIG. 14 is a flowchart illustrating an example of a process of calculating the ray numbers of the sub-pixels (ray number calculation process). As illustrated in FIG. 14, first in step S201, the second acquiring unit 62 acquires the position of a viewer. In step S202, the correcting unit 90 corrects the panel parameters so that the position of the viewer acquired in step S201 is contained in the viewing zone. In step S203, the third calculating unit 103 calculates ray numbers of the sub-pixels with corrected panel parameters.

The image processing unit 400 according to the second embodiment performs the ray number calculation process described above in a predetermined cycle. Then, the three-dimensional image display device according to the second embodiment generates a three-dimensional image of the acquired three-dimensional data by using the ray numbers of the sub-pixels calculated by the ray number calculation process described above. The method for generating a three-dimensional image is the same as that described with reference to FIG. 9.

While certain embodiments have been described, these embodiments described above have been presented by way of example only, and are not intended to limit the scope of the inventions. Indeed, the novel systems, devices, methods and programs described herein may be embodied in a variety of other forms; furthermore, various omission, substitutions and changes in the form of the systems and programs described herein may be made without departing from the spirit of the inventions.

For example, in the embodiments described above, the ray control element unit 52 is arranged so that the extending direction of the optical openings 53 thereof has a predetermined slope with respect to the Y direction (column direction) of the panel (display element unit 51), and the magnitude of the slope can be arbitrarily changed. Alternatively, the ray control element unit 52 may have a structure (a so-called vertical lens) in which the extending direction of the optical openings 53 thereof is coincident with the Y direction of the panel, for example. The embodiments and the modification can also be arbitrarily combined.

The image processing unit (40, 400) in the embodiments described above has a hardware configuration including a CPU (central processing unit), a ROM, a RAM, a communication I/F unit, etc. The functions of respective components described above are implemented by expanding and executing various programs stored in the ROM on the RAM. Alternatively, at least part of the functions of the components can be implemented by an individual circuit (hardware). The image processing unit (40, 400) in the embodiments described above corresponds to an "image processing device" in the claims.

Alternatively, the programs to be executed by the image processing unit (40, 400) according to the embodiments described above may be stored on a computer system connected to a network such as the Internet, and provided by being downloaded via the network. Alternatively, the programs to be executed by the image processing unit (40, 400) according to the embodiments described above may be provided or distributed through a network such as the Internet. Still alternatively, the programs to be executed by the image processing unit (40, 400) in the embodiments described above may be embedded on a ROM or the like in advance and provided therefrom.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing device that generates a three-dimensional image to be displayed on a display unit including a display element unit that has pixels each containing a plurality of sub-pixels arranged thereon and a ray control element unit that controls emission directions of rays emitted from the sub-pixels, the image processing device comprising:
a first acquiring unit configured to acquire three-dimensional data for generating the three-dimensional image, the three-dimensional data being represented by a space partitioning model or a boundary representation model; and
a generating unit configured to calculate luminance values for each of the sub-pixels on the basis of the three-dimensional data and emission directions of a ray emitted from the sub-pixels through the ray control element unit, wherein
the generating unit includes
a first calculating unit configured to calculate ray information for identifying a rendering ray, for each of the sub-pixels on the basis of the emission direction, the rendering ray being a ray passing through a viewpoint associated with the sub-pixel and being used to calculate the luminance value of the sub-pixel, and
a second calculating unit configured to calculate the luminance value of the sub-pixel by using the ray information and the three-dimensional data for each of the sub-pixels, and
the generating unit identifies, for each of the sub-pixels, a viewpoint corresponding to a direction obtained by correcting a direction represented by the emission direction according to a coordinate system in which the three-dimensional data is defined, as a viewpoint of the sub-pixel.

2. The device according to claim 1, wherein the second calculating unit calculates, for each of the sub-pixels, the luminance value of the sub-pixel on the basis of color information of a portion where a rendering ray identified by the ray information and the three-dimensional data intersect.

3. The device according to claim 1, wherein the three-dimensional data is medical imaging volume data.

4. The device according to claim 1, wherein
the three-dimensional data includes a combination of a reference image representing an image associated with at least one viewpoint and depth data representing depth values of pixels of the reference image, and
the generating unit translates the reference image according to the emission direction of the sub-pixel and the depth data, and calculates the luminance values of the sub-pixel on the basis of the reference image resulting from a parallel translation.

5. The device according to claim 1, further comprising:
a second acquiring unit configured to acquire a position of a viewer;
a correcting unit configured to correct a parameter relating to association between the display element unit and the ray control element unit so that the position of the viewer is in a viewing zone that enables the viewer to view the three-dimensional image; and
a third calculating unit configured to calculate the emission direction of each of the sub-pixels with the parameter corrected by the correcting unit.

6. A three-dimensional image display device comprising:
a display including
a display element unit having pixels each containing a plurality of sub-pixels arranged thereon, and
a ray control element unit configured to control emission directions of rays emitted from the sub-pixels, a three-dimensional image being displayed on the display;
a first acquiring unit configured to acquire three-dimensional data for generating the three-dimensional image, the three-dimensional data being
represented by a space partitioning model or a boundary representation model; and
a generating unit configured to calculate luminance values for each of the sub-pixels on the basis of the three-dimensional data and emission directions of a ray emitted from the sub-pixels through the ray control element unit, wherein
the generating unit includes
a first calculating unit configured to calculate ray information for identifying a rendering ray, for each of the sub-pixels on the basis of the emission direction, the rendering ray being a ray passing through a viewpoint associated with the sub-pixel and being used to calculate the luminance value of the sub-pixel; and
a second calculating unit configured to calculate the luminance value of the sub-pixel by using the ray information and the three-dimensional data for each of the sub-pixels, and
the generating unit identifies, for each of the sub-pixels, a viewpoint corresponding to a direction obtained by correcting a direction represented by the emission direction according to a coordinate system in which the three-dimensional data is defined, as a viewpoint of the sub-pixel.

7. An image processing method for generating a three-dimensional image to be displayed on a display including a display element unit that has pixels each containing a plurality of sub-pixels arranged thereon and a ray control element unit that controls an emission direction of a ray emitted from the sub-pixels, the method comprising:
acquiring three-dimensional data for generating the three-dimensional image, the three-dimensional data being represented by a space partitioning model or a boundary representation model;
calculating luminance values for each of the sub-pixels on the basis of the three-dimensional data and emission directions of a ray emitted from the sub-pixels through the ray control element unit, wherein
the calculating includes
calculating ray information for identifying a rendering ray, for each of the sub-pixels on the basis of the emission direction, the rendering ray being a ray passing through a viewpoint associated with the sub-pixel and being used to calculate the luminance value of the sub-pixel, and
calculating the luminance value of the sub-pixel by using the ray information and the three-dimensional data for each of the sub-pixels; and
identifying, for each of the sub-pixels, a viewpoint corresponding to a direction obtained by correcting a direction represented by the emission direction according to a coordinate system in which the three-dimensional data is defined, as a viewpoint of the sub-pixel.

8. A computer program product comprising a non-transitory computer-readable medium containing a program for generating a three-dimensional image to be displayed on a display including a display element unit that has pixels each containing a plurality of sub-pixels arranged thereon and a ray control element unit that controls an emission direction of a ray emitted from the sub-pixels, the program causing a computer to execute:
acquiring three-dimensional data for generating the three-dimensional image, the three-dimensional data being represented by a space partitioning model or a boundary representation model;
calculating luminance values for each of the sub-pixels on the basis of the three-dimensional data and emission directions of a ray emitted from the sub-pixels through the ray control element unit, wherein
the calculating includes
calculating ray information for identifying a rendering ray, for each of the sub-pixels on the basis of the emission direction, the rendering ray being a ray passing through a viewpoint associated with the sub-pixel and being used to calculate the luminance value of the sub-pixel, and
calculating the luminance value of the sub-pixel by using the ray information and the three-dimensional data for each of the sub-pixels; and
identifying, for each of the sub-pixels, a viewpoint corresponding to a direction obtained by correcting a direction represented by the emission direction according to a coordinate system in which the three-dimensional data is defined, as a viewpoint of the sub-pixel.

* * * * *